United States Patent
Connolly

(10) Patent No.: US 10,682,145 B2
(45) Date of Patent: Jun. 16, 2020

(54) VASCULAR OCCLUSION DEVICES

(71) Applicant: Boston Scientific Scimed, Inc., Maple Grove, MN (US)

(72) Inventor: Joseph Michael Connolly, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 294 days.

(21) Appl. No.: 15/040,537

(22) Filed: Feb. 10, 2016

(65) Prior Publication Data

US 2016/0228128 A1  Aug. 11, 2016

Related U.S. Application Data

(60) Provisional application No. 62/114,488, filed on Feb. 10, 2015.

(51) Int. Cl.
*A61B 17/12* (2006.01)
*A61B 17/00* (2006.01)

(52) U.S. Cl.
CPC .. *A61B 17/12172* (2013.01); *A61B 17/12031* (2013.01); *A61B 17/12109* (2013.01); *A61B 17/12177* (2013.01); *A61B 2017/00336* (2013.01); *A61B 2017/00849* (2013.01); *A61B 2017/00893* (2013.01); *A61B 2017/12063* (2013.01); *A61B 2017/12095* (2013.01)

(58) Field of Classification Search
CPC ........ A61B 17/12172; A61B 17/12031; A61B 17/12109; A61B 2017/00893; A61B 2017/00849; A61B 2017/00336; A61B 17/12177; A61B 2017/12063; A61B 2017/12095

USPC .......................................... 606/200, 195, 198

See application file for complete search history.

(56) References Cited

U.S. PATENT DOCUMENTS

| | | | |
|---|---|---|---|
| 6,152,144 A | 11/2000 | Lesh et al. | |
| 8,641,777 B2* | 2/2014 | Strauss | A61L 31/022 623/23.72 |
| 2003/0181942 A1* | 9/2003 | Sutton | A61B 17/0057 606/200 |
| 2007/0067021 A1 | 3/2007 | Haverkost et al. | |
| 2011/0054515 A1 | 3/2011 | Bridgeman et al. | |
| (Continued) | | | |

FOREIGN PATENT DOCUMENTS

| | | |
|---|---|---|
| CN | 102395323 A | 3/2012 |
| WO | 2014008460 A2 | 1/2014 |

*Primary Examiner* — Vy Q Bui

(57) ABSTRACT

Various aspects of the disclosure pertain to blood vessel occlusion devices having a central longitudinal axis and comprising: (a) a hub, (b) a self-expanding support frame comprising a plurality of wire segments forming a plurality of cells, and (c) a covering material covering cells within the transition portion. The support frame may be self-expandable from a constrained shape to an unconstrained shape that comprises (ii) a substantially cylindrical portion having a diameter and an axis that is coincident with the central longitudinal axis, the substantially cylindrical portion comprising a first ring of the cells extending in a 360° rotation around the central longitudinal axis and (ii) a transition portion disposed between the substantially cylindrical portion and the hub. Other aspects for the disclosure pertain to assemblies, kits and methods that employ such devices.

18 Claims, 3 Drawing Sheets

(56) References Cited

U.S. PATENT DOCUMENTS

| | | |
|---|---|---|
| 2012/0330348 A1 | 12/2012 | Strauss et al. |
| 2013/0138138 A1 | 5/2013 | Clark et al. |
| 2014/0074151 A1* | 3/2014 | Tischler .................. A61F 2/01 606/200 |
| 2014/0135817 A1 | 5/2014 | Tischler et al. |
| 2014/0155980 A1* | 6/2014 | Turjman .......... A61B 17/12031 623/1.12 |
| 2014/0243882 A1 | 8/2014 | Ma |
| 2014/0350523 A1 | 11/2014 | Dehdashtian et al. |
| 2015/0005810 A1* | 1/2015 | Center ..................... A61F 2/01 606/200 |
| 2016/0158038 A1* | 6/2016 | Teitelbaum ............... A61F 2/90 623/1.11 |

* cited by examiner

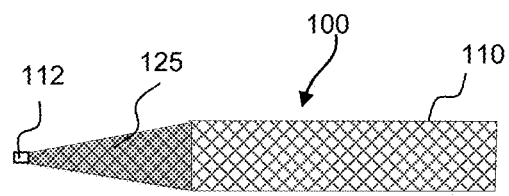
Fig. 4
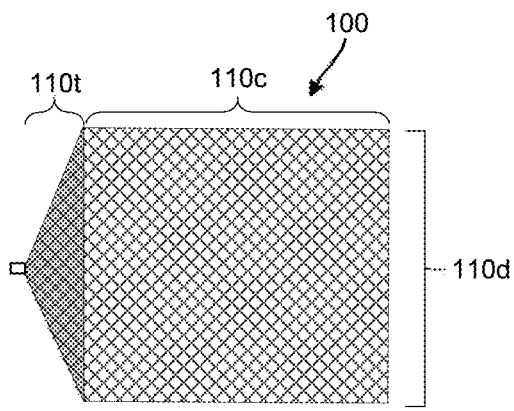
Fig. 4A
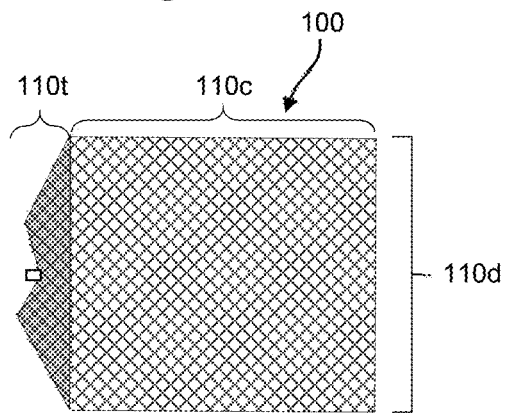
Fig. 4B
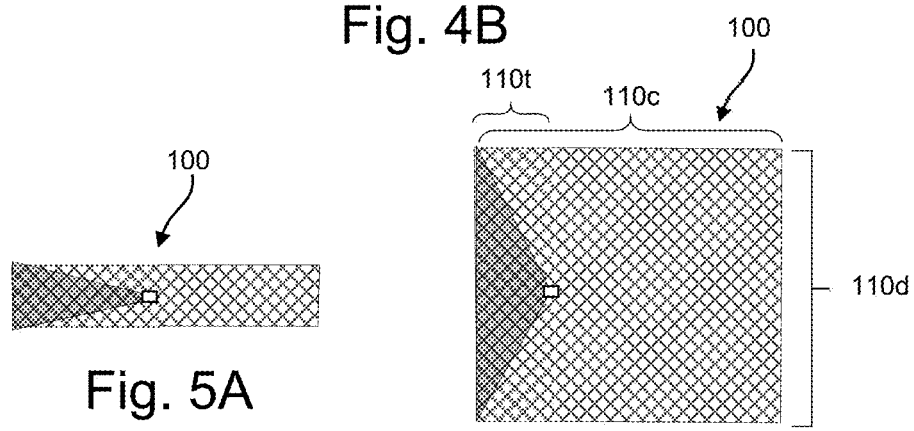
Fig. 5A
Fig. 5B

VASCULAR OCCLUSION DEVICES

CROSS-REFERENCE TO RELATED APPLICATIONS

This application claims the benefit of U.S. Provisional Application No. 62/114,488, entitled "Vascular Occlusion Devices" and filed Feb. 10, 2015, which is hereby incorporated by reference in its entirety.

FIELD

This application relates generally to devices, assemblies and kits for creating vascular occlusions and to methods for creating vascular occlusions using the same.

BACKGROUND

The endovascular treatment of a variety of conditions throughout the body is an increasingly important form of therapy. Blood vessel occlusion devices are known which are placed within the vasculature of the body in order to form a physical barrier to blood flow and/or promote thrombus formation at the site.

The present disclosure pertains to improved devices, assemblies, kits and methods for blood vessel occlusion.

SUMMARY

Various aspects of the disclosure pertain to blood vessel occlusion devices having a central longitudinal axis and comprising: (a) a hub, (b) a self-expanding support frame comprising a plurality of wire segments forming a plurality of cells, and (c) a covering material covering cells within the transition portion. The support frame may be self-expandable from a constrained shape to an unconstrained shape that comprises (ii) a substantially cylindrical portion having a diameter and an axis that is coincident with the central longitudinal axis, the substantially cylindrical portion comprising a first ring of the cells extending in a 360° rotation around the central longitudinal axis and (ii) a transition portion disposed between the substantially cylindrical portion and the hub.

In various embodiments, which may be used in combination with any of the above aspects and embodiments, the first ring of the blood vessel occlusion device may comprise from four to eight cells.

In various embodiments, which may be used in combination with any of the above aspects and embodiments, the substantially cylindrical portion of the blood vessel occlusion device may further comprise a second ring of the cells extending in a 360° rotation around the central longitudinal axis.

In various embodiments, which may be used in combination with any of the above aspects and embodiments, the transition portion of the blood vessel occlusion device has an axis that is coincident with the central longitudinal axis and comprises an additional ring of the cells extending in a 360° rotation around the central longitudinal axis.

In various embodiments, which may be used in combination with any of the above aspects and embodiments, the first ring of the cells, the second ring of the cells, or both, may comprise substantially diamond shaped cells, substantially hexagonal cells, or a combination thereof, and the additional ring of the cells may comprise substantially kite-shaped cells.

In various embodiments, which may be used in combination with any of the above aspects and embodiments, the plurality of cells of the blood vessel occlusion device may comprise a plurality of polygonal cells. The polygonal cells may be selected, for example, from quadrilateral cells and six-sided cells, among other possibilities.

In various embodiments, which may be used in combination with any of the above aspects and embodiments, the transition portion of the blood vessel occlusion device may comprise a substantially conic portion.

In various embodiments, which may be used in combination with any of the above aspects and embodiments, the hub of the blood vessel occlusion device may comprise an attachment feature. The attachment feature may, for example, comprise a threaded male member or a threaded female receptacle, among other possibilities.

In various embodiments, which may be used in combination with any of the above aspects and embodiments, the blood vessel occlusion device may further comprise a plurality of anchors arranged in at least one row about the circumference of the support frame.

In other aspects, the present disclosure pertains to assemblies that comprise (a) a blood vessel occlusion device in accordance with any of the above aspects and embodiments and (b) an elongated delivery member that is configured to be attached to and detached from the blood vessel occlusion device. For example, the elongated delivery member and the blood vessel occlusion device may comprise a threaded male member and a threaded female receptacle, or the elongated delivery member and the blood vessel occlusion device may comprise interlocking arms, among other possibilities.

In further aspects, the present disclosure pertains to kits that comprise (a) a blood vessel occlusion device or assembly in accordance with any of the above aspects and embodiments and (b) a tubular delivery device. For example, the tubular delivery device may be a catheter or a delivery sheath, among other possibilities.

In various embodiments, which may be used in combination with any of the above aspects and embodiments, the blood vessel occlusion device is compressed and preloaded into the tubular device in the constrained shape.

In still other aspects, the present disclosure pertains to methods of treatment that comprise (a) introducing a blood vessel occlusion device in accordance with any of the above aspects and embodiments into a blood vessel while in the constrained shape and (b) removing a constraint that maintains the blood vessel occlusion device in the constrained shape such that the support frame self-expands, the substantially cylindrical portion contacts a wall of the blood vessel, and the covering material impedes flow through the blood vessel.

In various embodiments, which may be used in combination with any of the above aspects and embodiments, the constraint may be removed by ejecting the blood vessel occlusion device from a tubular medical device.

In various embodiments, which may be used in combination with any of the above aspects and embodiments, the blood vessel may be selected from arteries, for example, a gastroduodenal artery, a hypogastric artery, a splenic artery, a renal artery, a right gastric artery and a left gastric artery, among others, or selected from veins, for example, gonadal veins, or pathologic veins such as gastroesophageal varices, among others.

The blood vessel occlusion devices, assemblies, kits and methods described herein are advantageous for use in a variety of procedures in that they are configured to form an embolus with only a single deployment and in that they have enhanced anchorability and a short "landing zone" (i.e., the length of blood vessel wall required for effective occlusion), while at the same time resisting kickback into a parent artery (e.g., when placed at a blood vessel ostium).

These and other aspects, embodiments and advantages of the present disclosure will become immediately apparent to those of ordinary skill in the art upon review of the detailed description and claims to follow.

BRIEF DESCRIPTION OF THE DRAWINGS

FIG. 4 is a schematic side view illustrating an occlusion device in accordance with an embodiment of the present disclosure in a constrained configuration;

FIGS. 4A and 4B are schematic side views illustrating the occlusion device of FIG. 4 in two alternative unconstrained configurations;

FIG. 5A is a schematic side view illustrating an occlusion device in accordance with another embodiment of the present disclosure in a constrained configuration; and FIG. 5B is a schematic side view illustrating the occlusion device of FIG. 5A in an unconstrained configuration.

DETAILED DESCRIPTION

A more complete understanding of the present disclosure is available by reference to the following detailed description of numerous aspects and embodiments of the disclosure. The detailed description which follows is intended to illustrate but not limit the disclosure.

The terms "proximal" and "distal" generally refer to the relative position, orientation, or direction of an element or action, from the perspective of a clinician using the medical device, relative to one another. Thus, "proximal" may generally be considered closer to the clinician or an exterior of a patient, and "distal" may generally be considered to be farther away from the clinician, along the length or beyond the end of the medical device.

The present disclosure pertains to devices, assemblies and kits for creating blood vessel occlusions. The occlusion devices of the present disclosure are collapsible to fit within a tubular device such as a catheter or delivery sheath and, when removed from the tubular device, can naturally expand toward an unconstrained configuration to fully occlude a blood vessel. For example, in certain embodiments the occlusion devices may be pushed through and/or from the distal end of a catheter (e.g., ranging from 0.021" (0.53 mm) microcatheter to a 5 French (1.67 mm) guide catheter) that is in place at the site of embolization. Upon exiting the catheter, the device will automatically expand to the diameter of the blood vessel, occluding the same.

Figure 1:
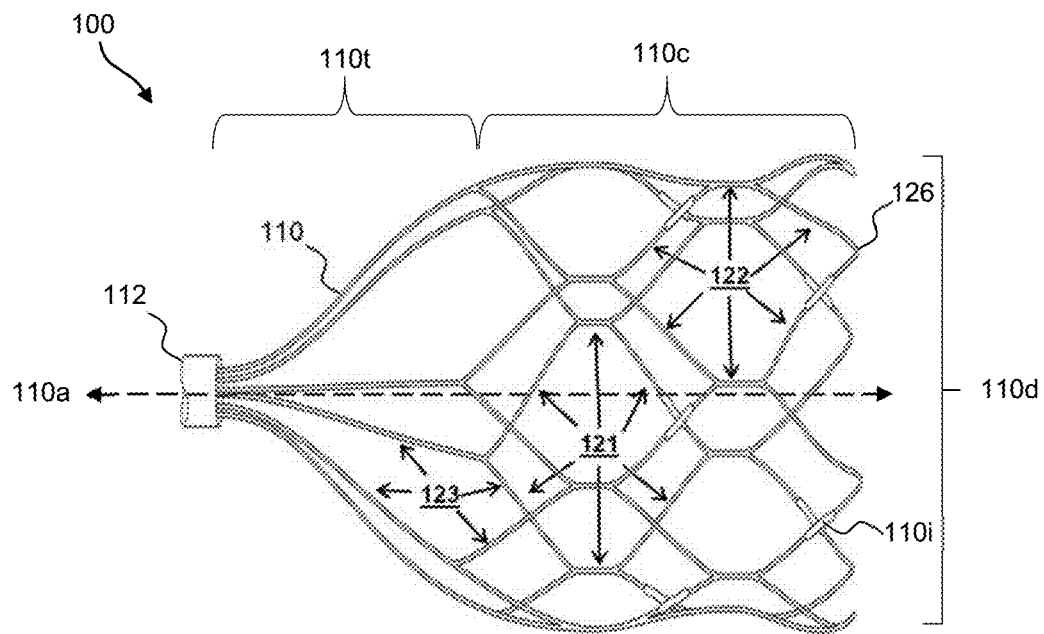
FIG. 1 is a schematic side view of a self-expanding support frame and hub of an occlusion device in accordance with an embodiment of the present disclosure.
Figure 2:
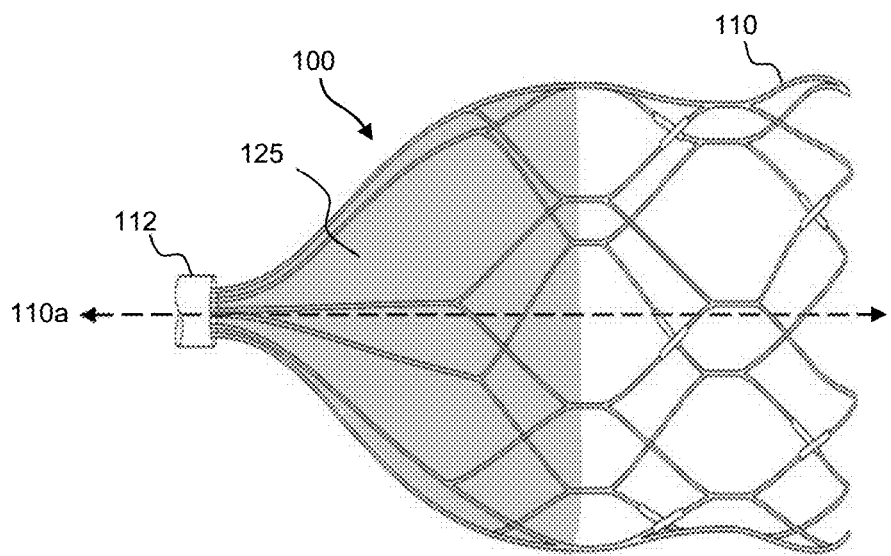
FIG. 2 is a is a schematic side view of an occlusion device in accordance with an embodiment of the present disclosure.

FIGS. 1 and 2 illustrate a blood vessel occlusion device 100 in an unconstrained uncovered state (FIG. 1) and an unconstrained covered state (FIG. 2) in accordance with the present disclosure. The blood vessel occlusion device 100 may have a central longitudinal axis 110a and may generally comprise a support frame 110 having an axis 110a and a hub 112 attached to the support frame 110 at a proximal end of the device 100. The hub 112 may include an attachment feature, for example, mechanical attachment feature (e.g., an interlocking member such as a male or female threaded member or other interlocking member) or an electrolytically dissolvable attachment feature, for attachment to and detachment from an elongate delivery member as discussed below. The hub may also be provided with radiopaque characteristics as discussed below. The support frame 110 may comprise a plurality of wire segments forming a mesh that comprises a plurality of closed cells (i.e., a plurality of wire segments forming a closed loop). The support frame 110 may comprise a substantially cylindrical portion 110c (e.g., a portion having a variation in diameter of 25% or less, beneficially 20% or less, more beneficially 10% or less, along the axial length of the portion), having a diameter 110d and an axis coincident with the longitudinal axis 110a of the occlusion device 100, and a transition portion 110t disposed between the substantially cylindrical portion 110c and the hub 112. In the embodiment shown, the support frame 110 comprises a substantially conic transition portion 110t disposed between the substantially cylindrical portion 110c of the support frame 110 and the hub 112. Like the substantially cylindrical portion 110c, transition portion 110t has an axis coincident with the longitudinal axis 110a.

In the embodiment shown, wire segments form a mesh comprising numerous polygonal cells. In this regard, the support frame 110 may include a plurality of wire segments forming a first ring of polygonal cells 121 (one numbered, with arrows pointing to the wire segments), more particularly, a first ring of generally diamond-shaped cells, even more particularly, a first ring of hexagonal cells in which two shortened wire segments form opposing sides. The first ring of polygonal cells 121 extend in a 360° rotation around the axis 110a of the occlusion device 100. The support frame 110 further includes a second ring of polygonal cells 122 (one numbered, with arrows pointing to the wire segments), more particularly, a second ring of generally diamond-shaped cells, even more particularly a second ring of hexagonal cells in which two shortened wire segments form opposing sides. Like the first ring of polygonal cells 121, the second ring of polygonal cells 122 extend in a 360° rotation around the axis 110a of the occlusion device 100. The first and second rings of polygonal cells each form substantially cylindrical portions of the support frame in the embodiment shown, each having a diameter 110d and an axis coincident with the longitudinal axis 110a. Collectively the first and second rings of polygonal cells form the substantially cylindrical portion 110c of the support frame 110. At the distal end of the support frame 110, pairs of wire segments form intersection points 126. In the embodiment shown, the pairs of wire segments curve radially inward at the distal end of the device, thereby assisting with insertion of the device into a lumen of a blood vessel (e.g., into an ostium of a blood vessel).

The support frame 110 may also include a plurality of wire segments forming a third ring of polygonal cells 123 (one numbered, with arrows pointing to the wire segments), more particularly a third ring of quadrilateral cells, even more particularly a third ring of kite-shaped cells, extending in a 360° rotation around the axis 110a of the occlusion device 100. The third ring of polygonal cells 123 form the transition portion 110t of the support frame, more particularly, a substantially conic transition portion of the support frame 110, disposed between the hub 112 and the substantially cylindrical portion 110c of the support frame 110 that is formed by the first and second rings of polygonal cells 121, 122. The substantially conic transition portion 110t may be somewhat more convex than a perfect conic shape as shown or may be somewhat more concave (e.g., more trumpet-shaped in nature) than a perfect conic shape.

In the embodiment shown, the support frame 110 includes imaging markers 110i, for example, radiopaque markers. In other embodiments, imaging markers may be positioned at points where the wire segments of the support frame 110 intersect, among various other possibilities.

Although rings of six cells are provided in a 360° rotation around the axis 110a of the occlusion device 100 in the embodiment shown, frames may be formed having any number of cells greater than two. Typically, the support frames 110 in accordance with the present disclosure have rings formed from four to eight cells in a 360° rotation around the axis 110a of the occlusion device 100. Moreover, although two rings of polygonal cells 121, 122 form a substantially cylindrical portion 110c of the support frame in the embodiment shown, other numbers of rings (e.g., one, three, four, etc.) may be employed to create the substantially cylindrical portion 110c. Furthermore, while the cells formed by the wire segments are substantially quadrilateral (e.g., kite-shaped and diamond-shaped) in the embodiment shown, one of ordinary skill in the art will recognize that support frames may be formed based on various other geometries.

As shown in FIG. 2, the blood vessel occlusion device 100 may comprise a covering 125 at least partially covering the support frame 110, which may assist the device in slowing or immediately halting blood flow upon expansion of the support frame in a blood vessel. In the embodiment shown, the covering 125 covers the cells 123 in the transition portion, as well as a portion of each cell 121 in the first ring of the substantially cylindrical portion 110c. This allows the covering 125 to substantially block flow of blood while at the same time leaving at least a portion of the wire segments in the first zone and the second zone exposed and thus better able to engage surrounding tissue. In some embodiments, the covering 125 may be permeable to blood and/or other fluids, such as water. In some embodiments, the covering 125 may be impermeable to such fluids. In some embodiments, a covering 125 may be selected that promotes endothelialization after implantation.

In various embodiments, the blood vessel occlusion device 100 may have an expanded diameter that is 20-50% greater than the diameter of a vessel to be embolized such that radial force assists in anchoring the device 100. Anchoring may also be assisted by pressure associated with the direction of blood flow in various embodiments.

In certain embodiments, at least the outer tissue-engaging surfaces of the wire segments of the support frame 110 (e.g., surfaces of the wire segments in the support frame 110 that are not covered by the covering 125 in the substantially cylindrical portion 110c of the device 100 shown in FIG. 2) may be roughened to better engage surrounding tissue, for example, where there is concern that the radial force exerted by the device (and blood flow in some cases) will not be adequate to sufficiently anchor the device. Alternatively or in addition, in certain embodiments the occlusion device may include a plurality of anchors (e.g., barbs, hooks, etc.) extending radially outward from the support frame such that they can engage tissue and inhibit longitudinal movement of the deployed blood vessel occlusion device. For instance, the support frame may be provided with a plurality of hooks or barbs around its circumference (e.g., hooks or barbs may be present in one or more rings around a circumference of a device 100 like that shown in FIG. 2, typically within the substantially cylindrical portion 110c of the support frame 110).

In various embodiments, the blood vessel occlusion devices described herein may be delivered via a tubular device (e.g., a catheter or a sheath inserted through a catheter) having an inner diameter ranging from 8% to 20% of the expanded diameter of the blood vessel occlusion devices.

For example, a blood vessel occlusion device having a compressed diameter sufficiently small to occupy a 0.021 inch inner diameter catheter (i.e., less than 0.021 inch or 0.53 mm) may have an unconstrained diameter ranging from 3 mm to 6 mm. Such devices are, for example, suitable for embolization of a vessel having an inner diameter ranging from 2 mm to 4 mm. Such a device may have from four to six cells around its circumference, among other possibilities.

A blood vessel occlusion device having a compressed diameter sufficiently small to occupy a 0.027 inch inner diameter catheter (i.e., less than 0.027 inch or 0.69 mm) may have an unconstrained diameter ranging from 6 to 8 mm. Such devices are, for example, suitable for embolization of a vessel having an inner diameter ranging from 3.5 mm to 8 mm. Such a device may have from four to six cells around its circumference, among other possibilities.

A blood vessel occlusion device having a compressed diameter sufficiently small to occupy a 5 French inner diameter catheter (i.e., 1.67 mm) may have an expanded diameter ranging from 8 mm to 15 mm. Such devices are, for example, suitable for embolization of a vessel having an inner diameter ranging from 8 mm to 13 mm. Such a device may have from four to eight cells around its circumference, among other possibilities.

In some embodiments, the support frame may be formed of or comprise a metallic material, a metallic alloy, a ceramic material, a polymer, a metallic-polymer composite, a ceramic-polymer composite, combinations thereof, and the like. Some specific examples of suitable materials may include metallic materials and/or alloys such as nickel-titanium alloy (nitinol) (e.g., super elastic or linear elastic nitinol), stainless steel (e.g., 303, 304 v, or 316L stainless steel), nickel-chromium alloy, nickel-chromium-iron alloy, cobalt alloy, nickel, titanium, platinum, and the like. In various embodiments, the hub may be formed from such materials as well.

Support frames may be formed from these and other materials by various methods. For example, in certain embodiments, a support frame may be cut from a tubular member, such as a metallic hypotube, or other suitable starting substrate. In some embodiments, the support frame may be laser cut from a single tubular member. The skilled artisan will recognize that various manufacturing methods known in the art may be used including, but not limited to, machining, chemical etching, water cutting, EDM, etc. In some embodiments, the support frame may be formed in a mold from a melted material. In some embodiments, a hub may be integrally formed with the support frame. In some embodiments, after forming the support frame, a plurality of free proximal ends of the support frame may be fixedly attached to a hub. For instance, a plurality of free proximal ends may be fixedly attached to a hub, for example, by adhesive(s), welding or soldering, friction fit, or other mechanical means. In some embodiments, the hub is provided with a male or female threaded member.

In some embodiments, the plurality of wire segments forming the support frame may be mixed with, doped with, coated with, wrapped with, or otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to metals such as gold, platinum, palladium, tantalum, and tungsten, metal alloys comprising one or more of the preceding metals, bismuth subcarbonate, iodine and the like. Such radiopaque materials may be formed in at certain points around the circumference of the support frame, for example, radiopaque makers may be positioned as shown in FIGS. 1 and 2, among other possibilities. The hub may also be formed from, coated with, wrapped with, or otherwise include a radiopaque material.

In some embodiments, the covering may be formed of or include a polymeric material, a metallic or metallic alloy material, a metallic-polymer composite, combinations thereof, and the like. In some embodiments, the covering is beneficially formed of polyethylene terephthalate (PET) such as DACRON®, polytetrafluoroethylene (PTFE), including expanded polytetrafluoroethylene (ePTFE), a polyamide such as nylon, or a polyurethane. Suitable polymers may further include a polyether-ester such as ARNITEL®, a polyester such as HYTREL®, a linear low density polyethylene such as REXELL®, a polyamide such as DURETHAN® available from Bayer or CRISTAMID® available from Elf Atochem, an elastomeric polyamide, a block polyamide/ether, a polyether block amide (PEBA) such as that available under the trade name PEBAX®, silicones, polyethylene, Marlex high-density polyethylene, polyetheretherketone (PEEK), polyimide (PI), and polyetherimide (PEI), alone or blended together. In some embodiments, the covering may be porous. In some embodiments, the covering may be formed using variety of suitable fiber-based fabrication techniques including, for example, various woven and non-woven techniques (e.g., knitting, braiding, electrospinning, electrospraying, etc.).

A covering formed from these and other materials may be attached to the support frame by various methods. In some embodiments, the support frame may include a plurality of barbs or other anchors, which may project through the covering holding it in place. In some embodiments, the covering may be attached to the support frame by other suitable attachment means, such as adhesive(s), sutures or thread(s), welding or soldering, or combinations thereof, among other possibilities. In some embodiments, a hole may be formed in the center of a covering material and the support frame placed concentrically within it. The support frame and covering may then be placed in the hub, with the covering material being fixed between the support frame and the hub.

In some embodiments, the blood vessel occlusion device may be coated with, or may otherwise include a material that provides a smooth, slick outer surface. In some embodiments, the blood vessel occlusion device may include or be coated with a lubricious coating, a hydrophilic coating, a hydrophobic coating, a drug-eluting material, or other suitable coating depending on the intended use or application.

In some embodiments, blood vessel occlusion devices are provided in conjunction with a delivery system that includes an elongate delivery member and tubular delivery device.

Figure 3A:
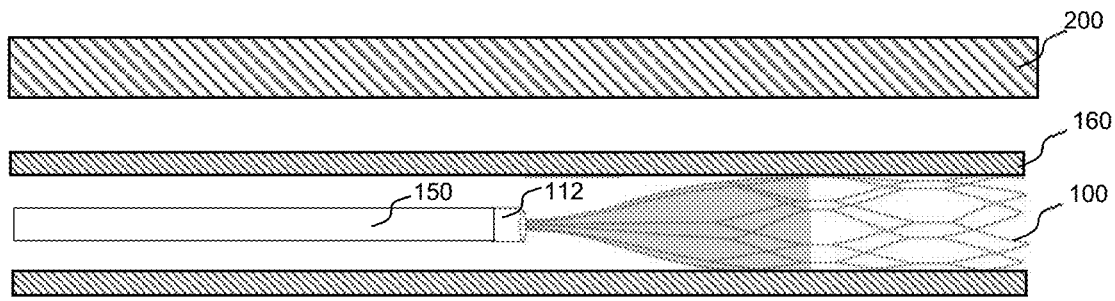
FIGS. 3A-3C are schematic partial cross-sectional views showing the deployment in the vasculature of an occlusion device in accordance with an embodiment of the present disclosure.
Figure 3B:
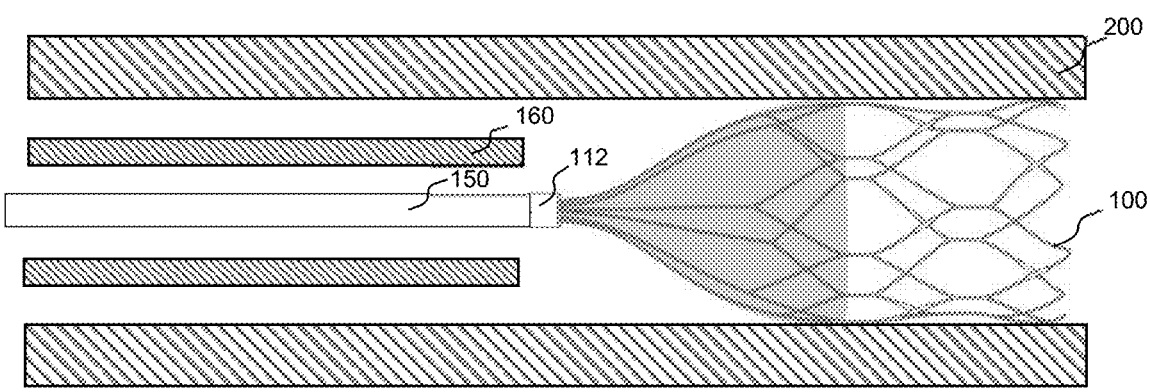

With reference to FIGS. 3A and 3B, for delivery, the blood vessel occlusion device 100 may be compressed within a lumen of a tubular device such as a delivery catheter 160, in a constrained position. An elongate delivery member such as a delivery shaft 150 may also be disposed within the lumen of the delivery catheter 160 and may be reversibly connected to the blood vessel occlusion device 100 at the proximal hub 112, such that the blood vessel occlusion device 100 can be advanced and withdrawn relative to the catheter 160 as desired and eventually released within the body. For example the delivery shaft 150 may comprise a threaded male fitting at its distal end which is threaded into a female threaded fitting within the hub 112, among various other possible mechanical (e.g. interlocking arms, etc.) and electrical (e.g., electrolytic dissolution, etc.) means of forming such a reversible connection. The delivery catheter 160, blood vessel occlusion device 100 and delivery shaft 150 collectively form a delivery system.

The delivery system may be percutaneously inserted into a patient to deliver the blood vessel occlusion device 100 to a desired vascular site 200 (e.g., an artery, vein, etc.). Access to an artery or vein to be embolized may be achieved via the femoral artery, femoral vein, or radial artery, among other access points. Initially, the blood vessel occlusion device 100 may be disposed in a first, constrained position within the lumen of the delivery catheter 160, as shown in FIG. 3A.

Figure 3C:
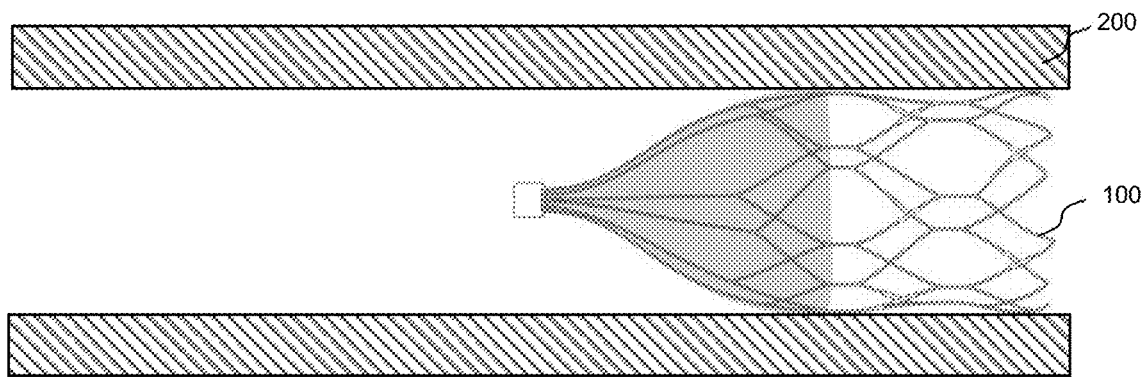

Upon reaching the desired delivery location, the delivery catheter 160 may be withdrawn proximally while keeping the delivery shaft stationary, or the delivery shaft 150 may be advanced distally while the delivery catheter 160 is held stationary (i.e., relative movement between the delivery catheter and the delivery shaft 150 is created), such that the blood vessel occlusion device 100 emerges from the delivery catheter 160 and self-expands radially outward to an expanded position where the support frame may extend radially outward such that the outer surface of the blood vessel occlusion device 100 conforms to the wall of the vascular site 200 as shown in FIG. 3B. Lastly, delivery shaft 150 may be disconnected from the proximal hub 112 and the delivery catheter 160 and delivery shaft 150 removed from the patient, leaving the blood vessel occlusion device at the vascular site 200 as shown in FIG. 3C. Once implanted, the covering acts to slow or halt the blood flow. In some embodiments, the entire device may act as a substrate for coagulation, creating a permanent embolus. In certain beneficial embodiments, the device becomes integrated to the vascular tissue. In some embodiments, the covering material physically blocks blood flow (e.g., where the covering material is non-porous or has very small pores), without relying on a coagulation cascade to form the blockage (cf., embolic coils and other devices which require a coagulation cascade to form a blockage). This is advantageous for patients with coagulopathies (e.g. patients having dysfunction clotting cascades such that clots do not readily form).

Using these and other procedures, the blood vessel embolization devices described herein may be implanted into a wide variety of blood vessels to be embolized, including a wide variety of arterial and venous blood vessels. Examples of arteries in which the blood vessel embolization devices may be implanted include the following arteries (including any divisions thereof): internal iliac artery (hypogastric artery), external iliac artery, gastroduodenal artery, renal artery, hepatic artery, uterine artery, lienal artery, splenic artery, intercostals artery, mesenteric artery, right gastric artery, left gastric artery, lumbar artery, internal carotid artery, communicating artery, basilar artery, bronchial artery, cerebral artery, cerebellar artery, profunda femoris artery, gastroepiploic artery, and pancreaticoduodenal artery, among others. Examples of veins in which the blood vessel embolization devices may be implanted include a pelvic vein, internal iliac vein (hypogastric vein), portal vein and gonadal veins (e.g. spermatic vein or ovarian vein, depending on gender), among others. Examples of blood vessels in which the blood vessel embolization devices may be implanted further include abnormal blood vessels, for example, arteriovenous fistulas and arteriovenous malformations, among others.

In particularly beneficial embodiments, blood vessel embolization devices as described herein may be employed to perform prophylactic gastroduodenal artery embolization (the gastroduodenal artery is a branch of the common hepatic artery) and/or right gastric artery embolization, for example, prior to Y90 therapy or other microsphere therapy for hepatocellular carcinoma or liver metastases (e.g., drug eluting microspheres, TACE, etc.) as well as to perform prophylactic hypogastric embolization (the hypogastric artery is also known as the internal iliac artery) prior to AAA stent graft implantation. Each of these procedures require embolization of the ostium of an artery.

The blood vessel occlusion devices described herein are advantageous in these and other procedures in that they are configured to clot with only a single deployment and in that they have enhanced anchorability and a short "landing zone" (i.e., the length of blood vessel required for effective occlusion), while at the same time resisting kickback into a parent artery (e.g., when placed at a blood vessel ostium), due to the fact that they have a highly defined shape upon deployment (and due to the direction of blood flow in some embodiments).

Turning now to the idealized schematic illustrations of FIGS. 4, 4A and 4B, an occlusion device 100, having a hub 112, support frame 110 and cover 125 in accordance with the present disclosure, may be introduced into the vasculature of a patient in constrained state as schematically shown in FIG. 4. Upon removal of the constraining force, the occlusion device may expand into a variety of configurations. For example, analogous to the occlusion device of FIGS. 2 and 3A-3B, the occlusion device 100 may have a support frame 110 that is self-expandable from a first constrained shape shown in FIG. 4 to a second unconstrained shape shown in FIG. 4A, in which the support frame comprises a substantially cylindrical portion 110c having a diameter 110d and a substantially conic transition portion 110t disposed between the substantially cylindrical portion 110c and the hub 112. While the transition portion 110t in FIG. 4A is substantially conic in shape, myriad other shapes are possible, including a transition portion 110t like that shown in FIG. 4B, in which the transition portion necks inward from the cylindrical portion 110c in a proximal direction, then reverses direction to neck inward to the hub in a distal direction. While the transition portion is shown having a sharply angled transition in FIG. 4B, other more curvilinear transitions are also possible.

In FIGS. 4, 4A and 4B, the hub 112 of the device 100 is positioned proximal to substantially cylindrical portion 110c when in a constrained state. In other embodiments, the hub 112 of the device 100 may be within the substantially cylindrical portion 110c when in a constrained state as shown in FIG. 5A. Upon removal of the constraining force, the occlusion device may expand into a variety of configurations. For example, the occlusion device 100 of FIG. 5A may self-expand to an unconstrained shape shown in FIG. 5B, in which the support frame comprises a substantially cylindrical portion 110c having a diameter 110d and a substantially conic transition portion 110t disposed within the substantially cylindrical portion 110c.

In another aspect of the disclosure, medical kits useful in embolization procedures are provided. The medical kits may include all or a subset of all the components useful for performing the procedures. For example, the medical kits may comprise any combination of any two, three, four, or more of the following items: (a) a vessel occlusion device as described herein, (b) a tubular device (e.g., a catheter or sheath) suitable for delivering the vessel occlusion device (in certain beneficial embodiments, the vessel occlusion device may be compressed and preloaded into the tubular device in a constrained, i.e., reduced diameter, shape), (c) an elongate delivery member such as a delivery shaft, which may be reversibly connected to the blood vessel occlusion device via a suitable mechanism such as one of those described herein, (d) a catheter introducer, (e) suitable packaging material, and (f) printed material with one or more of the following: storage information and instructions regarding how to deploy the vessel occlusion device in a subject.

Although various embodiments are specifically illustrated and described herein, it will be appreciated that modifications and variations of the present disclosure are covered by the above teachings and are within the purview of the appended claims without departing from the spirit and intended scope of the disclosure.

The invention claimed is:

1. A body lumen occlusion device having a central longitudinal axis and comprising:
   (a) a hub,
   (b) a self-expanding support frame comprising a plurality of wire segments forming a plurality of cells, said support frame being self-expandable from a constrained shape to an unconstrained shape that comprises (i) a substantially cylindrical portion with an open end having a variable diameter and an axis that is coincident with the central longitudinal axis, said substantially cylindrical portion comprising a first ring of said cells extending in a 360° rotation around the central longitudinal axis and a second ring of said cells comprising hexagonal cells extending in a 360° rotation around the central longitudinal axis, the cells of the second ring each having two opposing sides shorter than remaining sides of each of the cells of the second ring such that the second ring comprises a diameter at the two opposing sides that is smaller than a diameter of the remainder of the second ring, and (ii) a transition portion comprising a third ring of said cells, the transition portion having a diameter less than the cylindrical portion and disposed between the substantially cylindrical portion and the hub, and
   (c) a covering material covering cells within the transition portion.

2. The body lumen occlusion device of claim 1, wherein the first ring comprises from four to eight cells.

3. The body lumen occlusion device of claim 1, wherein the transition portion has an axis that is coincident with the central longitudinal axis and the third ring of said cells extend in a 360° rotation around the central longitudinal axis.

4. The body lumen occlusion device of claim 3, wherein the first ring of said cells or both, comprise diamond shaped cells, hexagonal cells, and wherein the third ring of said cells comprises substantially kite-shaped cells.

5. The body lumen occlusion device of claim 1, wherein said plurality of cells comprise a plurality of polygonal cells including the hexagonal cells of the second ring.

6. The body lumen occlusion device of claim 5, wherein the polygonal cells are selected from quadrilateral cells and six-sided cells.

7. The body lumen occlusion device of claim 1, wherein the hub comprises an attachment feature.

8. The body lumen occlusion device of claim 7, wherein the attachment feature comprises a threaded male member or a threaded female receptacle.

9. The body lumen occlusion device of claim 1, further comprising a plurality of anchors arranged in at least one row about a circumference of the support frame.

10. An assembly comprising the body lumen occlusion device of claim 1 and an elongated delivery member that is configured to be attached to and detached from the body lumen occlusion device.

11. The assembly of claim 10, wherein the elongated delivery member and the body lumen occlusion device comprise a threaded male member and a threaded female receptacle or wherein the elongated delivery member and the body lumen occlusion device comprise interlocking arms.

12. A kit comprising a body lumen occlusion device and a tubular delivery device, said body lumen occlusion device having a central longitudinal axis and comprising:
(a) a hub,
(b) a self-expanding support frame comprising a plurality of wire segments forming a plurality of cells, said support frame being self-expandable from a constrained shape to an unconstrained shape that comprises (i) a substantially cylindrical portion with an open end having a variable diameter and an axis that is coincident with the central longitudinal axis, said substantially cylindrical portion comprising a first ring of said cells extending in a 360° rotation around the central longitudinal axis and a second ring of said cells comprising hexagonal cells extending in a 360° rotation around the central longitudinal axis, the cells of the second ring each having two opposing sides shorter than remaining sides of each of the cells of the second ring such that the second ring comprises a diameter at the two opposing sides that is smaller than a diameter of the remainder of the second ring, and (ii) a transition portion comprising a third ring of said cells, the transition portion having a diameter less than the cylindrical portion and disposed between the substantially cylindrical portion and the hub, and
(c) a covering material covering cells within the transition portion.

13. The kit of claim 12, wherein the body lumen occlusion device is compressed and preloaded into the tubular delivery device in said constrained shape.

14. The kit of claim 12, wherein the tubular delivery device is a catheter.

15. The kit of claim 12, further comprising an elongated delivery member that is configured to be attached to and detached from the body lumen occlusion device.

16. A method of treatment comprising:
introducing a body lumen occlusion device into a body lumen, said body lumen occlusion device having a central longitudinal axis and comprising:
(a) a hub,
(b) a self-expanding support frame comprising a plurality of wire segments forming a plurality of cells, said support frame being self-expandable from a constrained shape to an unconstrained shape that comprises (i) a substantially cylindrical portion with an open end having a variable diameter and an axis that is coincident with the central longitudinal axis, said substantially cylindrical portion comprising a first ring of said cells extending in a 360° rotation around the central longitudinal axis and a second ring of said cells comprising hexagonal cells extending in a 360° rotation around the central longitudinal axis, the cells of the second ring each having two opposing sides shorter than remaining sides of each of the cells of the second ring such that the second ring comprises a diameter at the two opposing sides that is smaller than a diameter of the remainder of the second ring, and (ii) a transition portion comprising a third ring of said cells having a concave portion, the third ring of said cells, the transition portion having a diameter less than the cylindrical portion and disposed between the substantially cylindrical portion and the hub, and
(c) a covering material covering cells within the transition portion and
removing a constraint that maintains the body lumen occlusion device in said constrained shape such that the support frame self-expands, the substantially cylindrical portion contacts a wall of the body lumen, and the covering material impedes flow through the body lumen.

17. The method of claim 16, wherein the constraint is removed by ejecting the body lumen occlusion device from a tubular medical device.

18. The method of claim 16, wherein the body lumen is selected from a gastroduodenal artery, a hypogastric artery, a splenic artery, a renal artery, a right gastric artery and a left gastric artery.

* * * * *